(12) United States Patent
Bäck et al.

(10) Patent No.: US 8,353,889 B2
(45) Date of Patent: Jan. 15, 2013

(54) HYGIENIC ARTICLE WITH TEMPORARILY ATTACHED SIDE PANELS

(75) Inventors: Lucas Bäck, Billdal (SE); Paulina Halleröd (neé Ljungberg), Göteborg (SE)

(73) Assignee: SCA Hygiene Products AB, Gothenburg (SE)

( * ) Notice: Subject to any disclaimer, the term of this patent is extended or adjusted under 35 U.S.C. 154(b) by 350 days.

(21) Appl. No.: 12/739,485

(22) PCT Filed: Nov. 8, 2007

(86) PCT No.: PCT/SE2007/050830
§ 371 (c)(1),
(2), (4) Date: Apr. 23, 2010

(87) PCT Pub. No.: WO2009/061244
PCT Pub. Date: May 14, 2009

(65) Prior Publication Data
US 2010/0262112 A1    Oct. 14, 2010

(51) Int. Cl.
*A61F 13/15*    (2006.01)
(52) U.S. Cl. ......... 604/385.11; 604/385.16; 604/385.28; 604/385.31; 604/387; 604/396; 604/391; 604/394
(58) Field of Classification Search ............. 604/385.11, 604/385.16, 385.28, 385.31, 387, 396, 391, 604/394
See application file for complete search history.

(56) References Cited

U.S. PATENT DOCUMENTS
4,568,344 A    2/1986 Suzuki et al.
(Continued)

FOREIGN PATENT DOCUMENTS
EP    0113464 A1    7/1984
(Continued)

OTHER PUBLICATIONS

Notification Concerning Transmittal of International Preliminary Report on Patentability (Forms PCT/IB/326 and PCT/IB/373) and the Written Opinion of the International Searching Authority (Form PCT/ISA/237) issued in corresponding International Application No. PCT/SE2007/050830 dated May 20, 2010.

(Continued)

*Primary Examiner* — Jacqueline F. Stephens
(74) *Attorney, Agent, or Firm* — Buchanan Ingersoll & Rooney PC

(57) ABSTRACT

A hygienic article having side panels extending outward in a lateral direction from either of said front or back waist region. Each side panel comprises at least two material segments which are connected to each other by a lap seam wherein said material segments define a distal segment and a proximal segment in the lateral direction. On the distal edge of each side panel a fastening member is placed which is capable of securing said side panels to the front or back waist region such that the hygienic article assumes a pant like shape. The material segments which form the side panels are attached to each other by the lap seam in such a way that when the side panels are folded back towards the longitudinal centerline of the hygienic article, the materials are attached to each other in the lap seam such that the most distal material segment is placed closer towards the inner or outer surface of the hygienic article than the more proximal material segment attached to said most distal segment. Furthermore, at least one temporary attachment is situated on the lap seam or between the lap seam and the longitudinal outer edge of the chassis.

13 Claims, 3 Drawing Sheets

U.S. PATENT DOCUMENTS

| | | | |
|---|---|---|---|
| 5,226,992 A | | 7/1993 | Morman |
| 5,376,430 A | | 12/1994 | Swenson et al. |
| 6,645,190 B1 | | 11/2003 | Olson et al. |
| 7,156,833 B2 * | | 1/2007 | Couture-Dorschner et al. ............... 604/387 |
| 2001/0042584 A1 | | 11/2001 | Karami et al. |
| 2003/0109844 A1 | | 6/2003 | Gibbs |
| 2004/0194260 A1 | | 10/2004 | Wendelstorf et al. |
| 2006/0287637 A1 | | 12/2006 | Lam et al. |

FOREIGN PATENT DOCUMENTS

| | | |
|---|---|---|
| EP | 0 646 062 A1 | 4/1995 |
| EP | 1 035 818 A1 | 9/2000 |
| EP | 1 133 967 A1 | 9/2001 |
| EP | 1 350 494 A1 | 10/2003 |
| EP | 1 418 874 A2 | 5/2004 |
| FR | 2724110 A1 | 3/1996 |
| GB | 2 257 895 A | 1/1993 |
| GB | 2 292 067 A | 2/1996 |
| JP | 63-309606 A | 12/1988 |
| JP | 11-511671 A | 10/1999 |
| JP | 2007-229198 A | 9/2007 |
| WO | WO 94/00292 A1 | 1/1994 |
| WO | WO 96/32084 A1 | 10/1996 |
| WO | WO 98/29251 A1 | 7/1998 |
| WO | WO 99/27876 A1 | 6/1999 |
| WO | WO 00/35398 A1 | 6/2000 |
| WO | WO 01/00129 A1 | 1/2001 |
| WO | WO 02/26183 A1 | 4/2002 |
| WO | WO 02/49567 A1 | 6/2002 |
| WO | WO 03/000165 A1 | 1/2003 |
| WO | WO 03/015683 A2 | 2/2003 |
| WO | WO 03/047488 A1 | 6/2003 |
| WO | WO 2007/071267 A1 | 6/2007 |

OTHER PUBLICATIONS

International Search Report of PCT/SE2007/050830 dated Jul. 24, 2008.

Written Opinion of the International Searching Authority of PCT/SE2007/050830 dated Jul. 24, 2008.

Office Action (Notice of Reasons for Rejection) dated Apr. 24, 2012, issued in correspoding Japanese Patent Application No. 2010-533034, and an English Translation thereof. (6 pages).

Extended European Search Report dated Jul. 9, 2012 issued in the corresponding European Patent Application No. 07835414.9.

* cited by examiner

HYGIENIC ARTICLE WITH TEMPORARILY ATTACHED SIDE PANELS

TECHNICAL FIELD OF THE INVENTION

The present invention relates to a hygienic article having an inner surface facing the user during use, an outer surface facing away from the user during use and optionally an absorbent core therebetween. The hygienic article also comprises a front waist region and a back waist region with a crotch region connecting said front and back waist regions along a longitudinal direction and has side panels extending outward in a lateral direction from either of said front or back waist region. Each side panel comprises at least two material segments which are connected to each other by a lap seam wherein said material segments define a distal segment and a proximal segment in the lateral direction. On the distal edge of each side panel a fastening member is placed which is capable of securing said side panels to the front or back waist region such that the hygienic article assumes a pant like shape. Said side panels are folded back towards the hygienic articles longitudinal centreline before use and attached to the inner or outer surface by at least one temporary attachment.

BACKGROUND ART

Absorbent products comprising side panels are today quite common on open absorbent articles and known to those skilled in the art. By using side panels instead of fastening tabs it is possible to make the chassis of the product narrower which saves both material cost as well as makes the product more pleasant to wear since the product doesn't cover as much of the users' skin. Another advantage is the fact that side panels can easily be tailored to have desired characteristics such as elasticity or breathability.

A drawback with side panels is the production problem. Absorbent products are produced at very high speeds and side panels extending outwards in a lateral direction can cause problems such as jamming of the machine with the material pieces. This problem can be overcome by temporarily attaching the loose distal ends of the side panels in the process, said attachments at a later stage being released by the user when putting on the article. Such temporary attachments are described in e.g. WO2007/071267 and WO02/26183.

As mentioned above, side panels can be tailored to have specific characteristics such as elasticity or breathability. Such side panels are often composed of at least two material segments. An advantage of combining different material segments is that elastic materials and breathable materials tend to be more expensive than simple nonwoven laminates and the amount of such expensive material used can thus be reduced. A further reason may be that elastic materials as well as breathable materials can have a poor shear strength and if a large material piece is used the side panel might not be able to withstand the forces induced in the panel during use. Examples of such side panels can be found in US 20030109844, EP 1133967 and WO 2002049567.

A common problem with these side panels is that the attachment between the different material segments can provide a weakness in the side panel construction. This is normally not a very large problem if the different material segments are attached to each other by lap seams, which means that the lap seams will be influenced by a shear force rather than a peel force when the article is used. A lap seam has generally higher resistance to breaking when subjected to shear forces than when subjected to peeling forces.

An absorbent article having side panels comprising two material segments where said side panel is temporarily attached during production and transportation is disclosed in EP 1 418 874. The material segments of the side panels are connected by lap seams and are folded in a Z configuration and temporarily attached in the Z configuration. When the user pulls the side panels outwards to release the temporary attachment, shear forces are achieved in both the lap seam and in the temporary attachments. If one desires to break an attachment it is advantageous to have a peel force since it is not as strong as a shear force if applied onto the same attachment. Thus, if a shear force is achieved in an attachment which is intended to break this will be a disadvantage since the direction of force is unfavourable and a higher force is required which might lead to tearing of the materials attached by said temporary attachments. There is also a certain complexity in the folding arrangement of the side panels which might cause production difficulties.

In view of these documents there is still a need for a product which has side panels comprising more than one material segment where the user doesn't risk tearing the materials attached by the temporary attachment when releasing the side panels or to break the lap seam attaching the two material segments together. At the same time the production process of articles with such side panels should be easy without too many complex processing steps.

SUMMARY OF THE INVENTION

The present invention provides a hygienic article having an inner surface facing the user during use, an outer surface facing away from the user during use and optionally an absorbent core therebetween; said hygienic article comprising a front waist region and a back waist region with a crotch region connecting said front and back waist regions along a longitudinal direction; said absorbent article comprising side panels extending outward in the lateral direction from either said front or back waist region; said side panels comprising at least two material segments which are connected to each other by a lap seam; said material segments defining a distal segment and a proximal segment in the lateral direction; said side panels each having at least one fastening member at their distal ends which fasteners are capable of securing said side panels to the front or back waist region such that the absorbent article assumes a pant like shape; said side panels are folded back towards the absorbent articles longitudinal centreline before use and attached to the inner or outer surface by at least one temporary attachment whereby the material segments which form the side panels are attached to each other by the lap seam in such a way that when the side panels are folded back towards the longitudinal centreline of the hygienic article the materials are attached to each other in the lap seam such that the most distal material segment is placed closer towards the inner or outer surface of the hygienic article than the more proximal material segment attached to said most distal segment and that at least one temporary attachment is situated on the lap seam or between the lap seam and the longitudinal outer edge of the chassis.

This placement ensures that when severing the temporary attachments a favourable load condition is achieved such that the force exerted on the lap seam will be essentially a shear force and not a peel force. At the same time the force needed to break the temporary attachments is a peel force which ensures that the materials attached by the temporary attachment will not break since a bond breaks easier when subjected to a peel force than to a shear force.

Another advantage is that the product only requires one folding step in the process which reduces the risk of machine jamming compared to when the side panels have been folded in a more complex manner. Thus according to another embodiment of the invention the side panels are only folded once in the lateral direction.

According to another embodiment of the invention each side panel comprises at least three material segments. This could be an advantage if it is desired to introduce a material into the side panels which is very expensive, allowing for a smaller piece to be used, alternatively the material introduced is not able to resist strong shear forces and a large material segment would thus cause a weakness in the side panel construction. Using three or more material segments thus allows for an improved tailoring of the side panel characteristics as compared to a side panel composed of only two material segments.

At least one of the material segments in a side panel may be a breathable material. Non-breathable materials tend to increase humidity in the area where the materials are placed in close proximity to the skin of a user. If a non-breathable material is replaced by a breathable material, said breathable materials are able to transport the moisture and humidity caused by perspiration away from the skin surface of the users. Breathable materials thus provide superior comfort to the users as compared to products which do not have breathable areas.

It is also possible to make at least one of the material segments in a side panel from an elastic material. Insertion of an elastic material into the side panels enables the hygienic product to better conform to the user when the user moves around. Since the diameter of the waist area greatly alters when sitting or standing, a piece of elastic material can ensure that the product doesn't slip down when a user stands up or causes red marks when the user sits down. Simply because a material is elastic it is not excluded that it can also be breathable, thereby combining the advantages of breathability and elasticity in the same side panel.

The fastening member of the side panel may be a hook fastener. Hook fasteners are advantageous to use since they allow for multiple opening and reclosing of the hygienic article without damaging the article. Most often a landing member is used onto which the hook fastener is attached but it is also possible to attach the hook fastener directly onto the outer surface of the hygienic article if said surface is made of a nonwoven material which can significantly reduce the cost of the hygienic article.

According to another embodiment of the invention the temporary attachments are placed between the fastening member situated on the most distal edge of the side panel and at least 1 cm from the longitudinal side edge of the chassis, preferably the placement should be between the fastening member and at least 3 cm from the longitudinal side edge of the chassis. This placement ensures that when a user pulls open the temporary attachments they can easily see if the side panels are completely released or if some temporary attachments still remain which need to be released. A problem associated with unreleased temporary attachments is that if the user puts on a product where a temporary attachment has not been released, said attachment is not designed to be sufficiently strong to withstand the pulling forces induced in the side panel during use. Thus, the unreleased temporary attachment will most probably release when the article is being worn and the product will slip down the users' waist. This might cause discomfort to the user and there is also a greater risk of leakage since the product is not kept properly in place.

According to a further embodiment of the invention a force of 0.5-10 N is required to rupture the temporary attachments, preferably a force of 0.5-7 N is required, more preferably a force of 1-5 N is required and most preferably a force of 2-3 N is required. The force is measured according to ASTM D 1876-72 on 25 mm wide samples. In order to withstand the forces in the production process and during transportation it is desired that the force necessary to break said temporary attachments should be at least 0.5 N. However, if the temporary attachments are too strong there is a risk of tearing the materials attached by said temporary attachments when the attachments are to be released. The force required to break said temporary attachments should thus preferably be 10N or lower.

According to an embodiment of the invention each side panel consists of three material segments where the most distal lap seam has the most distal material segment placed closer to the absorbent article than the more proximal material segment and the most proximal lap seam has the most proximal material segment placed closer to the absorbent article than the more distal material segment and where the temporary attachment is placed on the most distal lap seam or between the most distal lap and the most proximal lap seam.

BRIEF DESCRIPTION OF THE DRAWINGS

The invention will be described in greater detail below with reference to the embodiments shown in the appended drawings, in which.

DEFINITIONS

As used herein, "hygienic articles" refer to articles including absorbent articles and absorbent or non-absorbent holders for absorbent articles or absorbent inserts which may or may not be reusable.

"Absorbent articles" refer to diapers, incontinence articles, sanitary panties as well as any other similar product which is suitable to use for absorbing urine or menstrual fluids.

"Shear force" refers to a force which is applied to materials in a plane generally parallel to the plane of attachment of the materials.

"Peel force" refers to a force applied at an angle of 70 degrees or more to the attachment between the materials.

"Inner surface" is intended to mean a surface made up of any material on the surface of the hygienic article which is facing the user during use. Structural elements which are normally considered to be part of the inner surface in an absorbent article are topsheets and standing gathers.

"Outer surface" refers to the material forming the cover of the hygienic article which faces the user's garment during use. An outer surface is often referred to as a backsheet but could include other structural elements which form part of the outer surface of a hygienic article.

A "fastening member" is herein defined as a fastener which is capable of temporarily attaching the side panels to the outer surface of the absorbent article such that the article assumes a pant like shape.

Figure 7:
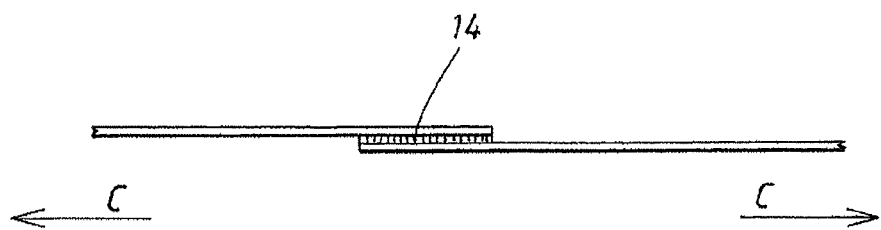
FIG. 7 shows a lap seam as intended by the present invention and when the material segments are pulled in different directions a shear force is induced in the lap seam attachment.
Figure 8:
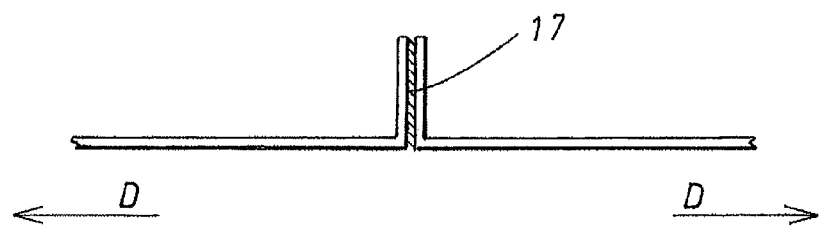
FIG. 8 shows an abutting seam which is not covered by the present invention and in which a peel force is induced in the abutting seam attachment when the two material segments are pulled in different directions.

By "lap seam" a fastening configuration is intended wherein the two material pieces are placed in an overlapping arrangement and thereafter permanently attached to each other. A permanent attachment is an attachment which is not intended to open during normal use and if it breaks, the attachment cannot be reattached. In FIG. 7 a lap seam is shown whereas the abutted seam in FIG. 8 is not intended to be covered by the definition lap seam.

A "side panel" is a portion of the article which extends in a lateral direction beyond one or both the longitudinal side edges of the chassis in one of the waist areas of the hygienic article.

The chassis is defined as the part of the hygienic article which comprises both outer surface material as well as inner surface material.

A "temporary attachment" is an attachment which is sufficiently strong to withstand a pulling force which might arise during, for example production and shipping, whilst at the same time being sufficiently weak to easily break without damaging the materials which are attached by said attachment. When a temporary attachment is released it cannot be reattached.

DETAILED DESCRIPTION

Figure 1:
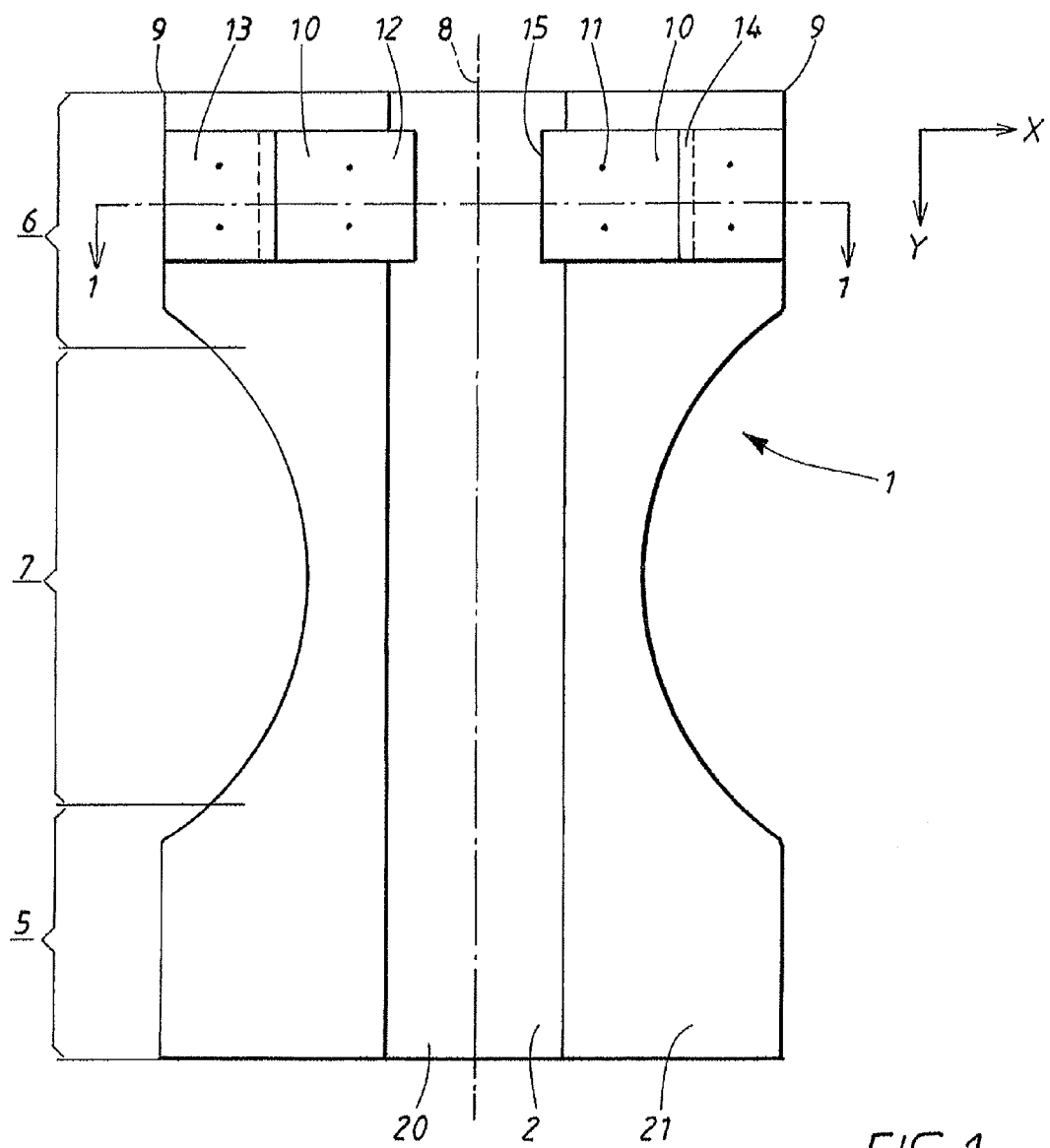
FIG. 1 shows an absorbent article according to one embodiment of the invention from the side intended to be directed towards a user during use.

FIG. 1 shows a diaper 1 seen from the inner side which is the side of the diaper intended to face the user during use of the diaper. The diaper 1 comprises an inner surface 2 and an outer surface 3 with an absorbent core 4 situated between the two surfaces. The diaper has a longitudinal direction y and a lateral direction x. The diaper comprises a front region 5, a back region 6 and a crotch region 7 connecting said front and back regions in a longitudinal direction y. Side panels 10 are attached to the diaper along the longitudinal side edges 9 of the back region 6. The side panels 10 are folded inwards towards a longitudinal centreline 8 of the diaper and have temporary attachments 11 to the inner surface 2 of the diaper 1, the temporary attachments in the shown example being in the form of ultrasonic bonds. The side panels 10 are composed of two material segments 12, 13 which segments are connected by a lap seam 14 which is ultrasonically bonded. The temporary attachments 11 of the side panels 10 are placed in rows of two individual attachments along a lateral direction x of the side panels 10, where one of the rows is situated between the longitudinal outer edge 9 of the diaper and the lap seam 14 and the second row is situated between the lap seam 14 and the distal edge 15 of the side panel 10.

Figure 2:
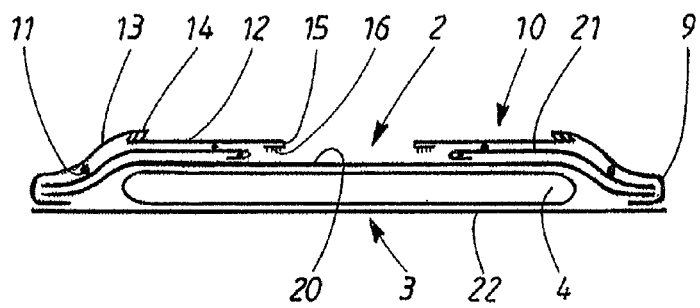
FIG. 2 shows a cross sectional view along the line 1-1 of FIG. 1.

FIG. 2 shows a cross sectional view along the line 1-1 of FIG. 1. The diaper in FIG. 2 shows a backsheet 22 (outer surface 3), a topsheet 20 (inner surface 2), standing gathers 21 (inner surface 2) and an absorbent core 4. Side panels 10 which each comprise two material segments 12, 13 are permanently attached to the diaper 1 between the topsheet 20 and the backsheet 22 materials and are folded inwards towards a longitudinal centreline 8 of the diaper 1. On the most distal edge 15 of the side panels 10 a hook member 16 is attached. The material segments 12, 13 forming the side panels 10 are attached to each other by the lap seam 14 in such a way that when the side panels 10 are folded in towards the longitudinal centreline 8 of the diaper 1 the materials 12, 13 are attached to each other in the lap seam 14 such that the most distal material segment 12 is placed closer towards the inner surface 2 of the diaper 1 than the more proximal material segment 13 attached to said most distal segment 12. The lap seam 14 connects the two materials segments 12, 13 by way of an ultrasonic bond. Temporary attachments 11 in the form of ultrasonic bonds are used to attach each side panel 10 in the folded configuration. As shown in FIGS. 1 and 2, the temporary attachments 11 are placed between the hook member 16 and the lap seam 14 as well as between the lap seam 14 and the longitudinal side edge 9 of the diaper chassis. In the example, the temporary attachments 11 form an attachment between the side panels 10 and standing gather material 21 found on the inner surface 2 of the diaper.

The inner surface 2 can comprise a typical topsheet material such as a nonwoven material, e.g. spunbond, meltblown, carded, hydroentangled, wetlaid etc. Suitable nonwoven materials can be composed of natural fibers, such as woodpulp or cotton fibres, man-made fibres, such as polyester, polyethylene, polypropylene, viscose, rayon etc. or from a mixture of natural and man-made fibres. The inner surface material 2 may further be composed of tow fibres, which may be bonded to each other in a bonding pattern, as e.g. disclosed in EP-A-1 035 818. Further examples of inner surface materials 2 are porous foams, apertured plastic films etc. The materials suited as inner surface materials 2 should be soft and non-irritating to the skin and if said inner surface is a topsheet 20 it should be readily penetrated by body fluid, e.g. urine or menstrual fluid. The inner surface may further be different in different parts of the absorbent article. Any part of the inner surface 2 that is constituted by a barrier structure such as a standing gather or a faeces pocket may be liquid-impermeable or at least show some degree of resistance to liquid penetration.

The outer surface 3 may be uniform or different in different parts of the hygienic article. At least in the area of the absorbent core 4, the outer surface 3 comprises a liquid impervious material, a thin plastic film, e.g. a polyethylene or polypropylene film, a nonwoven material coated to be a liquid impervious material, a hydrophobic nonwoven material, which resists liquid penetration, or a laminate of a plastic film and a nonwoven material. The outer surface material 3 may be breathable so as to allow vapour to escape from the absorbent core, while still preventing liquids from passing therethrough. Examples of breathable outer surface materials are porous polymeric films, nonwoven laminates of spunbond and meltblown layers and laminates of porous polymeric films and nonwoven materials. Preferably, the outer surface 3 comprises a nonwoven material on the garment-facing surface thereof to improve appearance and provide a more textile impression.

The "absorbent core" 4 is the absorbent structure disposed between the two surfaces 2, 3 of the absorbent article in at least the crotch region 7 thereof. The absorbent core 4 can be of any conventional kind. Examples of commonly occurring absorbent materials are cellulosic fluff pulp, tissue layers, highly absorbent polymers (so called superabsorbents), absorbent foam materials, absorbent nonwoven materials or the like. It is common to combine cellulosic fluff pulp with superabsorbent polymers in an absorbent core. Superabsorbent polymers are water-swellable, water-insoluble organic or inorganic materials capable of absorbing at least about 10 times their own weight of an aqueous solution containing 0.9 weight percent of sodium chloride. Organic materials suitable for use as superabsorbent materials can include natural materials such as polysaccharides, polypeptides and the like, as well as synthetic materials such as synthetic hydrogel polymers. Such hydrogel polymers include, for example, alkali metal salts of polyacrylic acids, polyacrylamides, polyvinyl alcohol, polyacrylates, polyacrylamides, polyvinyl pyridines, and the like. Other suitable polymers include hydrolyzed acrylonitrile grafted starch, acrylic acid grafted starch, and isobutylene maleic anhydride copolymers and mixtures thereof. The hydrogel polymers are preferably lightly cross-linked to render the material substantially water insoluble. Preferred superabsorbent materials are further surface cross-linked so that the outer surface or shell of the superabsorbent particle, fibre, flake, sphere, etc. possesses a higher crosslink density than the inner portion of the superabsorbent. The superabsorbent materials may be in any form which is suitable for use in absorbent composites including particles, fibres, flakes, spheres, and the like.

A high liquid storage capacity is provided by the use of high amounts of superabsorbent material. For an absorbent core 4 comprising a matrix of hydrophilic fibres, such as cellulosic fibres, and superabsorbent material, the proportion of superabsorbent material is preferably between 10 and 90% by weight, more preferably between 30 and 70% by weight.

It is conventional for absorbent articles to have absorbent cores comprising layers of different properties with respect to liquid receiving capacity, liquid distribution capacity and storage capacity. The thin absorbent bodies, which are common in for example baby diapers and incontinence guards, often comprise a compressed, mixed or layered structure of cellulosic fluff pulp and superabsorbent polymers. The size and absorbent capacity of the absorbent core 4 may be varied to suit different uses, such as infants or adult incontinent persons.

The absorbent core 4 may further include an acquisition distribution layer placed on top of the primary absorbent body, which is adapted to quickly receive and temporarily store discharged liquid before it is absorbed by the primary absorbent core. Such acquisition distribution layers are well known in the art and may be composed of porous fibrous wadding or foam materials. The side panels 10 are the material pieces which extend in a lateral direction x beyond the longitudinal side edges 9 of the chassis in one or both of the waist areas 5, 6 of the hygienic article. In this respect the chassis is intended as the part of the product which comprises at least one inner surface 2 and at least one outer surface 3, where said surfaces 2, 3 comprise different materials as discussed above. Accordingly, the side panels 10 may have a portion which comprises the outer surface material 3 which extends beyond the longitudinal side edge 9 of the inner surface material 2, or vice versa. The side panels 10 comprise at least two material segments 12, 13 extending in the lateral direction x.

The side panels 10 are for example made from a nonwoven material or a nonwoven material laminate. Preferably a soft nonwoven forms the inside of the panels which is intended to be in direct contact with the skin of the user.

A suitable nonwoven material can be a spunbond material of e.g. polypropylene or polyethylene fibres. Conjugate fibres may also be used. Another suitable nonwoven material is formed from a carded thermobonded material of e.g. polypropylene, polyester or conjugate fibres.

In a further embodiment at least one of the material segments forming the side panels 10 is breathable so as to allow vapour to escape from the surface of the skin of the user. Examples of breathable outer surface materials are microporous and/or perforated polymeric films, nonwoven laminates of spunbond and meltblown layers and laminates of microporous and/or perforated polymeric films and nonwoven materials.

In still a further embodiment at least one of the material segments forming the side panels 10 is an elastic web material, such as elastic film, an elastic nonwoven, an elastic laminate or the like. The elastic laminate may be a laminate of two or more nonwoven layers, two or more film layers or a combination of film and nonwoven layers.

The elastic film may be of any suitable elastic polymer, natural or synthetic. Some examples of suitable materials for the elastic film are low crystallinity polyethylenes, metallocene-catalyzed low crystallinity polyethylene, ethylene vinyl acetate copolymers (EVA), polyurethane, polyisoprene, butadiene-styrene copolymers, styrene block copolymers, such as styrene/isoprene/styrene (SIS), styrene/butadiene/styrene (SBS), or styrene/ethylene-butadiene/styrene block copolymer. Blends of these polymers may also be used as well as other modifying elastomeric or non-elastomeric materials.

Examples of elastic laminates suitable for forming said elastic regions are any elastic laminate known in the art. One group of elastic laminates are so called "stretch-bonded" laminates, in which the elastic layer is stretched in at least one direction before laminating it with one or more inelastic layers. After the tension is removed from the elastic layer it can freely retract to its untensioned state, and the inelastic layer(s) laminated thereto become gathered, giving a three-dimensional puckering.

Another group of elastic laminates are so called "neck bonded" laminates, which refer laminates in which an elastic material is bonded to a non-elastic material while the non-elastic member is extended under conditions reducing its width or necked. "Neck bonded laminate" refers to a composite material having at least two layers in which one layer is a necked, non-elastic layer and the other layer is an elastic layer. The layers are joined together when the non-elastic layer is in an extended condition.

A further group of elastic laminates are disclosed in for example WO/047488, in which inelastic nonwoven layers are laminated to an elastic film layer, and the laminate is stretched above the point of failure of the nonwoven materials, so that the inelastic layers break.

Examples of elastic laminates are described in EP-B-0 646 062, WO 98/29251, WO 03/000165 and U.S. Pat. No. 5,226, 992. Examples of commercially available elastic laminates are Fabriflex 306 from Tredegar, PK 6358 from Nordenia and GP 403 and GP 401 from Golden Phoenix Fiberweb.

Alternatively the elastic material segments comprise one or more elastic threads or strips contractably affixed between web material layers.

Side panels 10 which combine the elastic material segment with a breathable material segment are also envisioned in the present invention. The breathable segment in the side panels may be a separate material segment or the elastic material segment may in itself be breathable whereby the two characteristics are combined in one material segment.

On the most distal edge 15 of the side panels 10 a mechanical fastener 16 is placed which is able to engage with another element placed on the outer side 3 of the hygienic product in the waist region opposed to the waist region carrying the side panels. Hook-and-loop fasteners are the most commonly used fasteners today.

A "hook-and-loop fastener" refers to complementary fastening means having a "hook" portion and a "loop" portion and which are refastenable. The term "hook" as used herein refers to any element capable of engaging another element, the so called "loop" portion. The term "hook" is not limited to only "hooks" in a narrow sense, but rather encompasses any form of engaging elements, whether unidirectional or bi-directional. The term "loop" is likewise not limited to "loops" in a narrow sense, but also encompasses any structure capable of engaging with a "hook" fastener. Examples of "loop" materials are fibrous structures, like nonwoven materials. Hook-and-loop fasteners are for example available from Velcro, USA.

Alternatively the fastening member is an adhesive fastening member such as a tape tab, wherein the external surface of opposite belt member may be of a material to which the tape can adhere, as for example described in WO 01/00129.

Further examples of mechanical fasteners are button and holes or button loops, snap fasteners and the like. The buttons can either be fastened to the belt or to the garment.

The lap seam 14 can be either a single line of attachment, completely covering in the region where the materials are joined or it can be a plurality of dots which join the material segments together in their overlapping configuration. The shape of attachment is not essential to this invention but due to the permanent nature of the lap seam said seam should be sufficiently strong to withstand any shear forces exerted in the panel during normal use without breaking.

An important feature of the invention to accomplish the desired load condition when breaking the temporary attachments is the order in which the material segments making up each side panel have been attached to each other in the lap seams. Accordingly, it is critical that the material segments are placed in an order so that when seen in a direction towards the inner surface of the article, the folded-in side panels have a more distal segment of each side panel positioned beneath the contiguous segment of the side panel in the connecting lap seam. In the folded-in configuration of the side panels that is shown in FIGS. 1-6, the most distal segment of each side panel will be the segment that is placed closest to the longitudinal centre line 8 of the article. Hence, this will be the material segment labelled 12 if FIGS. 1 and 2. Since the configuration of each lap seam 14 in FIGS. 1 and 2 is such, that the most distal material segment 12 is placed closer towards the inner 2 or outer surface 3 of the hygienic article 1 than the more proximal material segment 13 attached to said most distal segment 12 when the side panels 10 are folded in towards the longitudinal centreline 8 of the hygienic article 1, more favourable load conditions are achieved in the lap seam 14 when peeling apart the temporary attachments 11. These favourable load conditions differ from the prior art arrangements where the lap seam 14 was exposed to a peel force D instead of the shear force C arising in the arrangement according to the invention. Thus, the invention allows for the lap seam 14 to be less robust than was previously possible.

As can be seen in the experiments conducted below, the difference between the forces necessary to break an attachment by using shear force C instead of peel force D is about 75%, where the shear force C is about 75% stronger than the peel force D. In view of this, a lap seam 14 can be designed which is weaker than before. This means that both production time, for example quicker welding step, and material, for example less adhesive used, can be saved, thus reducing production costs. Moreover, a stronger seam is generally stiffer and less conformable than a weaker seam implying that the weld may cause comfort problems to a user of the hygienic article. However, it is preferred that the lap seam 14 is able to withstand the same forces as the material segments it combines without breaking. The type of attachment may be of any suitable type of bonding such as an adhesive, thermal, weld, ultrasonic, crimped or stitched bond.

The temporary attachments 11 according to various embodiments are intended to hold the side panels against the inner 2 or outer surface 3 of the hygienic article 1 during transportation. Temporary attachments 11 are such that they are sufficiently strong to withstand a pulling force which might arise, for example during production and shipping, whilst at the same time being sufficiently weak to easily break without damaging the materials which are attached by said attachment.

The temporary attachments 11 can be either a dot or a plurality of dots which hold the side panel 10 in place. In an alternative embodiment the temporary attachments 11 can be either a single line of attachment or it can be several lines along the lateral direction of the side panel. The type of attachment may be of any suitable type of bonding such as an adhesive, thermal, weld, ultrasonic or mechanical bonds such as crimping or needling.

The shape or type of the temporary attachment 11 is not essential to this invention as long as it is sufficiently strong to hold the side panels in place during production and transportation. However, the placement of the temporary attachment 11 is a very important feature of this invention.

Figure 5:
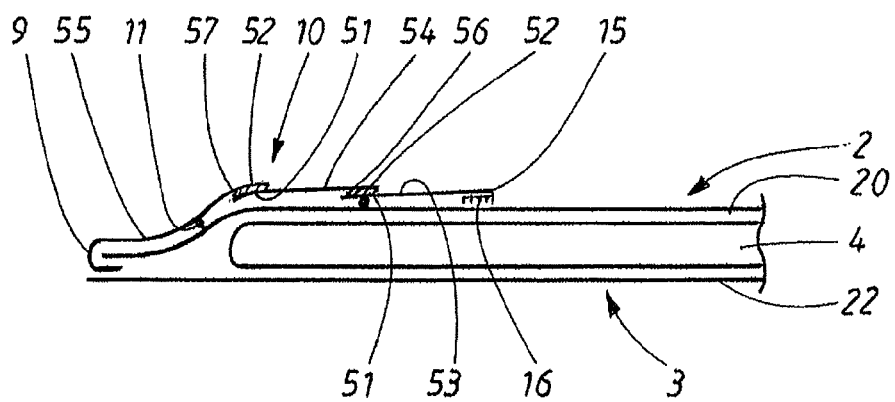
FIG. 5 shows a further embodiment according to the present invention where the side panel consists of three material segments.
Figure 6:
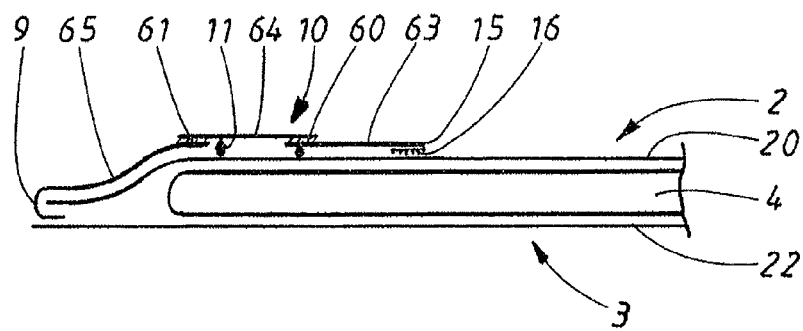
FIG. 6 shows still a an alternative embodiment according to the invention where the side panel consists of three material segments where the segments are placed a bit differently in relation to each other as compared to FIG. 5.

As previously mentioned at least one temporary attachment 11 should be placed on the lap seam 14 or between the lap seam 14 and the longitudinal outer edge of the chassis 9. This is applicable to all types of side panels 10 consisting of two or more material segments 12, 13, 53, 54, 55, as depicted in FIGS. 2 and 5, when the material segments 12, 13, 53, 54, 55 which form the side panels 10 are attached to each other by lap seams 14, 56, 57 in such a way that when the side panels 10 are folded in towards the longitudinal centreline 8 of the hygienic article 1 the materials 12, 13, 53, 54, 55 are attached to each other in the lap seams 14, 56, 57 such that the more distal material segment 12, 53, 54 is placed closer 51 towards the inner 2 or outer surface 3 of the hygienic article 1 in said lap seam 14, 56, 57 than the more proximal material segment 13, 54, 55 attached to said more distal segment 12, 53, 54. However, in an alternative embodiment, as depicted in FIG. 6, the three material segments 63, 64, 65 which form the side panels 10 are attached to each other by lap seams 60, 61 in such a way, that when the side panels 10 are folded back towards the longitudinal centreline 8 of the hygienic article 1 the materials 63, 64, 65 are attached to each other in the most distal lap seam 60 such that the most distal material segment 63 is placed closer towards the inner 2 surface of the hygienic article 1 than the central material segment 64 attached to said most distal segment 63, and in the more proximal lap seam 61 the most proximal material segment 65 is placed closer towards the inner 2 surface of the hygienic article 1 than the central material segment 64 attached to said most proximal material segment 65. In an embodiment such as the one depicted in FIG. 6, the temporary attachment 11 should be placed on the most distal lap seam 60 or on the central material segment 64.

If the side panel 10 has only one lap seam 14 or all lap seams 14 have the material segments 12, 13, 53, 54, 55 layered in the same manner as the most distal lap seam 14 then the placement of the temporary attachment 11 is not crucial. Even though it is not crucial to the invention, it has been found advantageous to place the temporary attachments 11 between the fastening member 16 situated on the most distal edge of the side panel 15 and at least 1 cm from the longitudinal side edge of the chassis 9, preferably the placement should be between the fastening member 16 and at least 3 cm from the longitudinal side edge of the chassis 9. This placement ensures that when a user pulls open the temporary attachments 11 they can easily see if the side panels 10 are completely released or if some temporary attachments 11 still remain which need to be released. A problem associated with unreleased temporary attachments 11 is that if the user puts on a product where a temporary attachment 11 has not been released or has not been completely released, said attachment 11 is not designed to be sufficiently strong to withstand the pulling forces induced in the side panel during use. Thus, the unreleased temporary attachment 11 will most probably release when the article is being worn and the product will slip down the users' waist. This might cause discomfort to the user and there is also a greater risk of leakage since the product is not kept properly in place.

As already mentioned, the temporary attachments 11 of any of the embodiments of the invention are restrained at least to an extent such that they withstand a pulling separating force which might arise, for example during shipping and manufacturing. On the other hand, they should be sufficiently loosely restrained so that they can easily be detached by a user without causing damage to the article or to the side panels themselves. To this end, any side panels 10 which comprise the releasable attachment 11 should be designed to be releasable under a force between about 0.5-10 N. It has been found that bonds or joins used for the temporary attachments 11 should have a separating strength exhibiting a minimum resistance of 0.5 N, in order to maintain product integrity during manufacturing and shipping, whilst user comfort and prevention of damage to the article is best ensured when forces below 10 N are needed for product deployment. These forces are intended to apply to an absolute pulling force applied to a 25 mm wide sample of a side panel 10 temporarily attached to a surface material 2, 3 where the two materials are pulled apart using a peel force D at a 90° angle to the bond or join location, as depicted in FIG. 8. Still preferably, the releasable attachments exhibit separating forces between 0.5-7 N, and still preferably between 1-5 N. A force of 2-3N or of approximately 2 N or approximately 3 N may be preferred. The strength of the temporary attachment 11 may vary for side panels 10 that are wider than 25 mm, but if it is possible to find a single 25 mm sample on the side panel 10, where the force necessary to break the temporary attachments 11 falls within the ranges defined above, it is considered to fall within the scope of the attachment forces defined. A test method to be employed for measuring the above delaminating separating forces may be according to ASTM D 1876-72.

Figure 3:
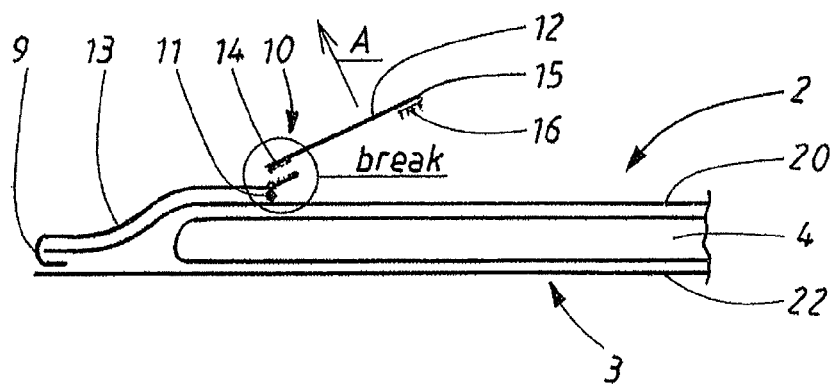
FIG. 3 shows an embodiment which is not part of this invention, the lap seam clearly breaks when the side panel is pulled to release the temporary attachment due to the unfavourable load condition caused by placing the distal segment farther away from the inner surface in the lap seam with respect to the proximal segment.

FIG. 3 shows an embodiment which is not according to the invention. In FIG. 3 the diaper 1 construction is the same as in FIG. 2 with the difference that the proximal segment 13 is placed closer to the inner surface 2 of the diaper 1 and the distal segment 12 is placed farther away from said surface in the lap seam 14. When the user pulls A the side panel 10 to release the temporary attachments 11, the lap seam 14 of the side panels breaks due to the unfavourable peel forces D in said attachment 14.

Figure 4:
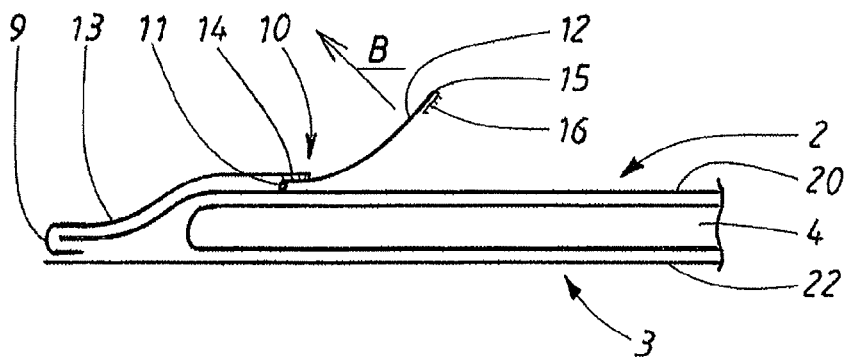
FIG. 4 shows an embodiment according to this invention, the lap seam does not break since the direction of the force in the lap seam differs from the one shown in FIG. 3 and hence a more favourable load condition is achieved.

FIG. 4 is the same type of construction as shown in FIG. 2. When the user pulls B the side panel 10 to release the temporary attachments 11, the force exerted in the lap seam 14 is a more favourable shear force C and said seam 14 does not break.

FIG. 5 shows an alternative embodiment of the present invention. In this figure a side panel is shown which has three material segments 53, 54, 55 along a lateral direction x of the diaper. The most distal segment 53 carries a hook fastener 16 and is placed closest towards the inner surface 2 of the diaper 1 in the lap seam 14. The more proximal middle section 54 comprises an elastic material and is placed further away 52 from the inner surface 2 of the diaper 1 than the most distal segment 53 in the most distal lap seam 56 but closer 51 towards the inner surface 2 than the most proximal segment 55 in the more proximal lap seam 57.

FIG. 6 shows a further embodiment according to the present invention. In this figure a side panel 10 is shown which has three material segments 63, 64, 65 along a lateral direction x of the diaper 1. The most distal segment 63 carries a hook fastener 16 and is placed closest towards the inner surface 2 of the diaper 1 in the lap seam 60. The more proximal middle section 64 comprises an elastic material and is placed farthest away from the inner surface 2 of the diaper 1 in both lap seams 60, 61. The temporary attachment 11 is placed on the most distal lap seam 60.

FIG. 7 shows a lap seam 14 according to the present invention.

FIG. 8 shows an abutting seam 17 which does not fall within the present invention.

Example

In order to show the difference in force C, D needed to separate two materials when using different pulling directions measurements were conducted.

Two different sets of 5 samples were prepared. The samples all consisted of two nonwoven spunbond material segments. The first material had a basis weight of 14 gsm and is an example of a material suitable as a surface material 2 on a hygienic article 1. The second material had a basis weight of 40 gsm and is an example of a material suitable as a side panel material 10 on a hygienic article 1. The two materials of all samples were attached to each other using a 2 mm wide line of hot melt adhesive. Of the samples five were attached with the materials in a lap seam 14 configuration as depicted in FIG. 7 which gives rise to shear forces C when the sample is pulled. The other set of five samples were attached with the materials in an abutting seam 17 configuration as depicted in FIG. 8 which gives rise to peel forces D when the sample is pulled. All ten samples were measured and cut into 25 mm wide material segments on which the tests were conducted.

The tests were conducted according to the test method ASTM D 1876-72 and measured on a tensile tester (any standard tensile tester can be used for the measurements).

The results of the test measurements were as follows:

Delamination of two layers, shear force C

| Sample number | Load at Peak (N) |
|---|---|
| 1 | 7.506 |
| 2 | 6.636 |

-continued

| Sample number | Load at Peak (N) |
|---|---|
| 3 | 6.628 |
| 4 | 7.466 |
| 5* | NA |
| 6 | 7.087 |
| Mean value | 7.065 |

*The nonwoven exemplifying a surface material broke before the lap seam, this sample was excluded Delamination of two layers, peel force D

| Sample number | Load at Peak (N) |
|---|---|
| 1 | 4.148 |
| 2 | 4.174 |
| 3 | 4.279 |
| 4 | 3.678 |
| 5 | 3.765 |
| Mean value | 4.009 |

As can be seen from the results, the force required to delaminate two materials attached by a lap seam 14 using a shear force C is about 75% higher than if a peel force D is used. These examples clearly show the advantage with the present invention in that the specific placement of the material segments in the lap seams 14 of the side panels 10 clearly reduces the risk of unwanted breakage in the lap seam.

Although only a few embodiments of the present invention have been shown and described, it is to be understood that many changes and modifications may be made thereto without departing from the scope of the invention as defined in the appended claims. Particularly, although the shown embodiments have the side panels folded in toward the inner surface of the hygienic article, it is to be understood that embodiments where the side panels are folded towards the outer surface and attached with temporary attachments are also within the scope of the invention.

The invention claimed is:

1. A hygienic article having an inner surface facing the user during use, an outer surface facing away from the user during use and optionally an absorbent core therebetween; said hygienic article comprising:
    a front waist region and a back waist region with a crotch region connecting said front and back waist regions along a longitudinal direction;
    side panels extending outward in a lateral direction from either said front or back waist region; each of said side panels comprising at least two material segments which are connected to each other by a lap seam; said material segments defining a distal segment and a proximal segment in the lateral direction; said side panels each having at least one fastener at their distal end which fasteners are adapted to secure said side panels to the front or back waist region such that the hygienic article assumes a pant like shape;
    said side panels are folded back towards the hygienic article longitudinal centreline before use and are attached to the inner or outer surface by at least one temporary attachment;
    wherein the material segments which form each side panel are attached to each other by the lap seam in such a way that when the side panels are folded back towards the longitudinal centreline of the hygienic article the distal material segment is placed closer towards the inner or outer surface of the hygienic article than the proximal material segment attached to said distal segment and that the at least one temporary attachment is situated on the lap seam or between the lap seam and the longitudinal outer edge of the chassis.

2. The hygienic article according to claim 1, wherein the side panels are only folded once in the lateral direction.

3. The hygienic article according to claim 1, wherein each side panel comprises at least three material segments.

4. The hygienic article according to claim 1, wherein at least one of the material segments in a side panel is a breathable material.

5. The hygienic article according to claim 1, wherein at least one of the material segments in a side panel is an elastic material.

6. The hygienic article according to claim 1, wherein the fastening member of the side panel is a hook fastener.

7. The hygienic article according to claim 1, wherein the temporary attachments are placed between the fastening member situated on the distal edge of the side panel and at least 1 cm from the longitudinal side edge of the chassis.

8. The hygienic article according to claim 7, wherein the placement is between the fastening member and at least 3 cm, from the longitudinal side edge of the chassis.

9. The hygienic article according to claim 1, wherein a force of 0.5-10 N is required to rupture the temporary attachments.

10. The hygienic article according to claim 1, wherein each side panel consists of three material segments where the most distal lap seam has the distal material segment placed closer to the hygienic article than the central material segment and the most proximal lap seam has the most proximal material segment placed closer to the hygienic article than the central material segment and wherein the temporary attachment is placed on the most distal lap seam or between the most distal lap seam and the most proximal lap seam.

11. The hygienic article according to claim 1, wherein a force of 0.5-7 N is required to rupture the temporary attachments.

12. The hygienic article according to claim 1, wherein a force of 1-5 N is required to rupture the temporary attachments.

13. The hygienic article according to claim 1, wherein a force of 2-3 N is required to rupture the temporary attachments.

* * * * *